United States Patent [19]  [11] 3,970,423
Brody et al.  [45] *July 20, 1976

[54] OXIDATIVE HAIR DYE COMPOSITIONS

[75] Inventors: Frederick Brody, New York; Stanley Pohl, New Rochelle, both of N.Y.

[73] Assignee: Clairol Incorporated, New York, N.Y.

[ * ] Notice: The portion of the term of this patent subsequent to May 20, 1992, has been disclaimed.

[22] Filed: Feb. 6, 1975

[21] Appl. No.: 547,675

Related U.S. Application Data

[62] Division of Ser. No. 186,475, Oct. 4, 1971, Pat. No. 3,884,627.

[52] U.S. Cl. ........................................ 8/10.2; 8/11
[51] Int. Cl.$^2$ ........................................ A61K 7/12
[58] Field of Search ................................ 8/10.2, 11

[56] References Cited
UNITED STATES PATENTS

| | | | |
|---|---|---|---|
| 2,162,458 | 6/1939 | Lehmann | 8/10.2 |
| 3,200,040 | 8/1965 | Lange | 8/10.2 X |
| 3,210,252 | 10/1965 | Blanke et al. | 8/10.2 |
| 3,582,253 | 6/1975 | Berth et al. | 8/10.1 |
| 3,884,627 | 5/1975 | Brody et al. | 8/10.2 |

Primary Examiner—Leonard Schenkman
Attorney, Agent, or Firm—Irving Holtzman; George A. Mentis; David J. Mugford

[57] ABSTRACT

Oxidative hair dye composition containing as "para component" compounds of the formula:

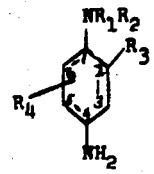

or their acid addition salts, in which:
 $R_1$ is alkyl or hydroxyalkyl;
 $R_2$ is hydrogen or hydroxyalkyl;
 $R_3$ is hydrogen, alkyl, alkoxy or halogen; and
 $R_4$ occupies any one of the remaining positions on the benzene radical and is hydrogen, alkyl, alkoxy or halogen; providing that $R_2$ is hydrogen when $R_3$ is alkyl, alkoxy or halogen and providing that at least two of $R_1$, $R_2$, $R_3$ or $R_4$ are other than hydrogen.

15 Claims, No Drawings

OXIDATIVE HAIR DYE COMPOSITIONS

This is a division of Application Ser. No. 186,475 filed Oct. 4, 1971 now U.S. Pat. No. 3,884,627.

This invention relates to oxidative hair dyeing mixtures containing certain p-phenylenediamine derivatives. More particularly, it concerns compositions of this character containing as para components compounds of formula:

I.

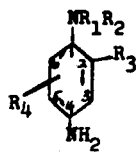

or their acid addition salts, in which:

$R_1$ is alkyl or hydroxyalkyl;
$R_2$ is hydrogen or hydroxyalkyl;
$R_3$ is hydrogen, alkyl, alkoxy or halogen; and
$R_4$ occupies any one of the remaining positions on the benzene radical and is hydrogen, alkyl, alkoxy or halogen; providing that $R_2$ is hydrogen when $R_3$ is alkyl, alkoxy or halogen and providing that at least two of $R_1$, $R_2$, $R_3$ or $R_4$ are other than hydrogen. In addition, this invention relates to certain of these p-phenylenediamine derivatives which are novel compounds.

It has long been a practice in the hair dyeing art to employ p-phenylenediamine or p-toluenediamine in hair dye compositions. These are ordinarily contained in so-called "oxidation dye mixtures" and are sometimes referred to as the "para components". They are dye intermediates rather than dyes, since their color must still be developed by reaction with another kind of dye intermediate called a "coupling component" also contained in the oxidation dye mixture by means of an oxidizing agent. The "oxidation dye mixture" is generally employed by mixing it with a solution of an oxidizing agent, generally hydrogen peroxide, just prior to the application of the "oxidation dye mixture" to the head. This serves to effect the oxidative coupling of the para components present with the coupling components, thereby producing a variety of colored products e.g. indamines or indophenols which contribute to the final shade imparted to the hair.

One chief disadvantage of the conventionally employed "para components" is that the colors developed by them with various coupling components undergo marked changes under conditions to which hair is ordinarily subjected. These developed colors do not show sufficient resistance to shampooing, do not exhibit good resistance to acid or alkaline perspiration and are not sufficiently fast to light. When these para components are used in hair dyeing compositions, the shades undergo very substantial changes in the strength and hue of dyeing. In particular, the shades become "warmer" or redder and the strengths weaken. It has been found that these disadvantages of the prior art "para components" tend, to a large degree, to be eliminated by employing compounds defined in Formula I above as the "para components".

It is accordingly an object of the present invention to provide oxidative hair dyeing compositions suitable for dyeing hair including "living" human hair which employ said para components.

It is also an object of the present invention to provide a method for dyeing hair which employs the aforesaid compositions.

It is a further object of the present invention to provide certain new para components for use in said compositions.

Other and more detailed objects of this invention will be apparent from the following description and claims.

Although Applicants do not want to be bound by any theory, it is their belief that the resistance to change exhibited by the colors developed by their para components, at least in the case of the preferred compounds, is due in large measure to the presence of (a) either two substituent groups on the amine nitrogen bonded to the number-1 carbon atom of the benzene ring in Formula I above, or (b) the presence of one substituent group on the amine nitrogen and one substituent ortho to the amine nitrogen on the aforesaid benzene ring. The presence of these substituents interferes sterically with the normal resonance of the resulting indamine and indophenol coupling products; in particular, their presence makes less probable the assumption of a quinoid structure by that ring bearing said substituents. This in turn makes less probable the further reaction of the indamines and indophenols (as by cyclization) to produce a change of color (generally to be redder than the original indamine or indophenol).

In those less favorable cases where there is only one substituent on the 1-amino group, and no substituent on the ring ortho to that group, there is no inhibition of resonance, but further reaction of the indophenols and indamines by cyclization is diminished when there is also a substituent $R_4$ in the meta-position (3- or 5- position in Formula I), since this is the position upon which cyclization occurs.

A few compounds, somewhat related to those defined in Formula I above, are known in the prior art as components of hair dyeing compositions. These, however, have certain disadvantages which make them unsuitable as hair dye components. Thus, for example, German Pat. No. 1,141,748 discloses N,N-dimethyl-p-phenylenediamine. This compound, although it shows advantages over p-phenylenediamine or p-toluenediamine, is unsuitable because of its toxicity. As a matter of fact, it is more toxic than the p-phenylenediamine which the present invention seeks to replace. In this connection, see Sax "Dangerous Properties of Industrial Materials" Reinhold, New York 1963. In contrast to this, the N,N-bis(2-hydroxyethyl)-p-phenylenediamine structurally related thereto and encompassed by the present invention has been found to be safe.

Belgium Pat. No. 649,310 and British Pat. No. 1,079,553 each discloses 2,6-dimethyl-p-phenylenediamine. This is an isomer of one of the species of the present invention; namely, N,2-dimethyl-p-phenylenediamine. The latter, however, has the distinct advantage of giving a bluish (violet) brown color when coupled with resorcinol, as compared with the less desirable yellowish brown color obtained with the prior art 2,6-dimethyl derivative. Resorcinol is a universal component of oxidation dye mixtures. Since the brown coupling product with resorcinol is the principal ingredient of the oxidized mixture, and the greatest contributor to the final shade, it is important that it be as blue as possible, in order to maintain the drabness of the shade as long as possible during wear. Moreover, it is common practice to add to oxidation dye mixtures a so called "meta components" (e.g. 2,4-diaminoanisole or 2,4-diaminotoluene) to provide a blue component on coupling. This is used for shading purposes and is known to be relatively unstable to wearing. By using N,2-diamethyl-p-phylenediamine as para component, in line with this invention, as distinguished from the 2,6-dimethyl derivative, a portion of the undesirable meta component may be eliminated since part of the blue color needed is supplied by the N,2-dimethyl-p-phenylenediamine resorcinol coupling product.

Any compound falling within the definition of Formula I above is suitable for the present purposes. When $R_1$, $R_2$, $R_3$ or $R_4$ is alkyl in said formula, it may be any of a variety of alkyl groups. Thus, it may be a straight chain or branched chain alkyl radical which is preferably lower alkyl, e.g. having from 1 to 6 carbon atoms. By way of illustration, the following alkyl groups may be mentioned as typical examples: methyl, ethyl, n-propyl, isopropyl, n-butyl, sec. butyl, tert. butyl, n-amyl, isoamyl, n-hexyl, and the like.

In the case where $R_1$, $R_2$, $R_3$ or $R_4$ is a hydroxyalkyl radical in Formula I, it may be a monohydroxy, dihydroxy, trihydroxy, or other polyhydroxyalkyl radical. The alkyl chain is preferably a lower alkyl chain having from 2 to 6 carbon atoms. Typical mono and polyhydroxyalkyl radicals of this character are 2-hydroxyethyl; 3-hydroxypropyl; 2-hydroxypropyl; tris(hydroxymethyl)methyl; 1,3-dihydroxy-2-methyl-propyl; 2,3-dihydroxypropyl; 1,3-dihydroxy-2-propyl, etc.

When $R_3$ or $R_4$ is halogen in Formula I, it can be any halogen atom, e.g. Cl, Br, I, or F. When it is alkoxy, the alkoxy group will usually contain 1 to 6 carbon atoms, e.g. methoxy, ethoxy, n-propoxy, isopropoxy, n-butoxy, n-amyloxy, isoamyloxy, isobutoxy, etc.

A large number of compounds that are useful as "para components" in compositions of the present invention are well-known compounds which can be prepared by any of a variety of known procedures. Their preparation is illustrated in examples below.

In addition a number of these "para components" are novel compounds. These may be described generally by the formula:

II 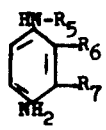

wherein:
a. $R_5$ is alkyl or hydroxyalkyl;
b. $R_6$ is hydrogen or alkyl; and
c. $R_7$ is hydrogen, alkyl, alkoxy or halogen providing that at least one of $R_6$ and $R_7$ is other than hydrogen and further providing that $R_6$ is not alkyl when $R_5$ is alkyl.

When $R_5$, $R_6$, or $R_7$ is alkyl in Formula II above it will usually be lower alkyl having 1 to 6 carbon atom e.g. methyl, ethyl, isopropyl, n-propyl, n-butyl, sec. butyl, tert. butyl, n-amyl, isoamyl, n-hexyl etc. When $R_5$, $R_6$ or $R_7$ is hydroxyalkyl in Formula II above it may be monohydroxy-, dihydroxy-, trihydroxy- or other polyhydroxyalkyl radical. The alkyl moiety of the hydroxyalkyl radical will ordinarily be a lower alkyl chain and will preferably contain from 2 to 6 carbon atoms. Typical hydroxyalkyl radical include 2-hydroxyethyl; 3-hydroxypropyl; tris(hydroxymethyl) methyl; 1,3-dihydroxy-2-methyl-propyl; 2,3-dihydroxypropyl and 1,3-dihydroxypropyl etc. When $R_7$ is alkoxy in Formula II above it will usually contain 1 to 6 carbon atoms, e.g. methoxy, ethoxy, n-propoxy, isopropoxy, n-butoxy, n-amyloxy, isoamyloxy, isobutoxy, etc. When it is halogen it may be Cl, Br, I, F.

In addition to using the para components in the form of their free bases, it is also possible in accordance with this invention to make compositions using the acid addition salts of these free bases. This is, in fact, desirable when the free base is inherently unstable to air oxidation. Among the acid salts which can be used one may mention the acid (hydrogen) sulfate, the neutral sulfate, the monohydrochloride, the dihydrochloride, the hydrobromide, the toluenesulfonate, the acetate, the citrate, the tartrate, and the like. In any case, whether the free base or its salt with an acid is used, the final pH of the composition is preferably adjusted so as to be alkaline, as hereinafter described, and the composition is essentially the same.

In preparing the "oxidaton dye mixture" of this invention one or more of the dye intermediates defined by said Formula I may be incorporated in the mixture. The quantity of dye intermediate, i.e. para component that corresponds to said formula which may be contained in these compositions may vary. Ordinarily, it will constitute in the free base form from between 0.1 and 6.0% by weight and preferably 0.2 to 4% based on the total weight of said "oxidation dye mixture." When the acid addition salt of the para component is used, the quantity will be larger depending on the particular salt used.

In addition to the para components used in this invention, other known para components may also be present, as for example p-toluenediamine, p-aminophenol, p-aminodiphenylamine, 4,4'-diaminodiphenylamine, p-phenylenediamine, 2,6-dimethyl-p-phenylenediamine, 2,5-diaminopyridine, and the like. Generally, when these are present the combined quantity of new and known para components will fall within the range mentioned above. In addition to para components, the hair dyeing compositions of this invention contain one or more coupling components, which react with the para compounds under oxidative conditions. These coupling components comprise a well-known class of compounds of the hair dye art which are known to react oxidatively (i.e. with the aid of an oxidizing agent) with para-diaminobenzene compounds to produce dyes.

A number of very different types of chemical compounds are known to function as coupling components. The most important are phenols, m-phenylenediamines, m-aminophenols and compounds containing active methylene groups.

Phenols react with para components, in the presence of oxidizing agents, to produce indophenols. These are usually blue or violet compounds, although resorcinols give yellow or brown colored compounds under these conditions. The brown colors obtained from the reaction of resorcinols are commonly used to produce the depth of a shade. Examples of phenols useful in oxidation dye compositions of this invention are pyrogallol, resorcinol, pyrocatechol and alpha-naphthol.

m-Phenylenediamines give indamines on oxidative coupling with para components and these are generally blue or violet compounds that can be used to modify a shade; usually they are employed to make a shade less warm. Examples of m-phenylenediamines commonly useful in the present oxidation dye compositions are m-phenylenediamine, 2,4-diaminoanisole and m-toluenediamine.

m-Aminophenols can give either indophenols or indamines on oxidative coupling with para components of this invention, however it seems likely that indophenols are the preferred product. The products are usually violet in color and are used in modifying shades. Examples of aminophenols useful herein are 2,4-diaminophenol, m-aminophenol, aminoresorcinol, 1,5-aminohydroxynaphthalene and 1,8-aminohydroxynaphthalene.

Compounds containing active methylene groups are also capable of reacting with the oxidatively activated para components. The products are imino compounds of various types and are yellow or red in color. Examples of active methylene compounds employable in the present invention are 3-methylpyrazolone-(5), 1-phenyl-3-methylpyrazolone-(5), 1,3-dimethylpyrazolone-(5), acetoacetic acid anilide, benzoylacetotoluide and nicotinoylacetanilide.

Still other oxidation dye intermediates may be present in the compositions of this invention which produce colored products under oxidative conditions by more complex mechanisms. This may include one or more self-coupling, or coupling with the para components or with other intermediates present. Among these may be mentioned hydroquinone, catechol, 1,5-naphthalenediol, o-phenylenediamine, o-aminophenol.

The quantity of coupling components and other dye intermediates contained in the oxidation dye mixture will vary depending on the shade desired. In general, the combined intermediates other than para will constitute between about 0.1 and 8% by weight based on the total weight of the oxidation dye mixture, and preferably between 0.1 and 4%.

It is sometimes desirable to add to said "oxidation dye mixture" dyes which are already colored i.e. which do not require an oxidizing agent for color development. These are generally added for blending purposes to obtain natural-looking colors in the final dyeing operation. One class of dyes which may be used for this purpose is the nitro dyes and this component is generally referred to herein as the "nitro dye component." A large number of nitro dyes are known in the prior art which are suitable for this purpose. The only limitation that is placed on a nitro dye to be useful in the present invention is that it be one whose color is not destroyed by the oxidizing agent used in the final color development of the oxidizable components. By way of illustrating suitable nitro dyes, mention may be made of the following: 4-nitro-o-phenylenediamine, 2-nitro-p-phenylenediamine, 4-nitro-2-aminophenol, 5-nitro-2-aminophenol, 2-nitro-4-aminophenol and picramic acid.

The quantity of "nitro dye component" i.e. single nitro dye or combination of nitro dyes which may be contained in the "oxidation dye mixtures" of this invention may also vary with the final color desired and the other components contained therein. Usually, however, when it is employed it will comprise from about 0.01 to 3.0% by weight of the "oxidation dye mixture" based on the total weight of said mixture, and preferably 0.01 to 2%.

In addition to the above components, the oxidation dye mixture of the present invention may contain other ingredients commonly found in prior art mixtures of this character. These include dispersing or surface active agents, soaps, solvents, thickeners, conditioning agents, alkaline agents, buffers, antioxidants, sequestering agents, perfumes, etc.

The pH of the oxidation dye mixture of this invention will generally be on the basic side e.g. 8–11. It is preferred, however, that this pH be in the range of about 9–10.

Any of a wide variety of alkalizing agents can be used to adjust the pH of the dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, such as ethylamine, or triethylamine; or alkanolamine, such as monoethanolamine or diethanolamine. Likewise, any other of the common alkalizing agents may be used, such as sodium or potassium hydroxide, sodium or potassium carbonate, sodium phosphate, sodium hydrogen phosphate, sodium silicate, and the like.

Among the soaps which may be present in the compositions of this invention may be mentioned the sodium, ammonium or potassium salts of lauric, stearic, palmitic, oleic, linoleic or ricinoleic acid. The soaps may be present to the extent of 5–35% of the weight of the oxidation dye mixture, and preferably, 15–25%.

Among the surface active agents useful in the present invention, mention may be made of the water-soluble surface-active agents. These can be anionic, non-ionic or cationic. Illustrative of the various types of water soluble surface active agents there can be mentioned: higher alkylbenzenesulfonates; alkylnaphthalenesulfonates; sulfonated esters of alcohols and polybasic acids; taurates; fatty alcohol sulfates; sulfates of branched-chain or secondary alcohols; alkyl dimethylbenzl ammonium chlorides; and the like. Illustrative of specific surfactants there can be mentioned; sodium lauryl sulfate; polyoxyethylene lauryl ester; myristyl sulfate; glyeryl monostearate; sodium salt of palmitic methyl taurine; cetyl pyridinium chloride; lauric diethanolamide; polyoxyethylene stearate; stearly dimethyl benzyl ammonium chloride; dodecyl benzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,9-diethyltridecanol-6-sulfate and the like. The quantity of water-soluble surface-active agent when present can vary over a wide range, such as that of from about 0.5 to 30% by weight of the composition, and preferably 1–10%.

Various organic solvents may also be present in the oxidation dye mixture for the purpose of solubilizing a dye intermediate or any other component which may be insufficiently soluble in water. Generally, the solvent selected is such as to be miscible with water and innocuous to the skin, and includes for example, ethanol, isopropanol, glycerine, ethylene glycol, propylene glycol, ethylene glycol monoethyl ether, diethylene glycol, diethylene glycol monoethyl ether, etc. The amount of solvent used may vary from 1–40% of the oxidation dye mixture, and preferably 5–30%.

To exemplify the thickening agents that can also be incorporated in the present dyeing composition, mention may be made of sodium alginate or gum arabic, or cellulose derivatives, such as methylcellulose, hydroxyethylcellulose, or the sodium salt of carboxymethylcellulose, or acrylic polymers, such as polyacrylic acid sodium salt, or inorganic thickeners, such as bentonite. The quantity of thickening agent when present can vary over a wide range, such as that of from about 0.5 to 5% and preferably from about 0.5 to 3% by weight.

To illustrate the antioxidants that may be used in the present oxidation dye mixture, mention may be made of sodium sulfite, thioglycollic acid, sodium hydrosulfite and ascorbic acid. The quantity of antioxidant that may be contained in the instant oxidation dye mixture will usually be in the range of from about 0.05 to 1% by weight based on the total weight of the oxidation dye mixture.

Water is ordinarily the major constituent of the present composition and can vary over a wide range dependent in large measure on the quantity of other additives. Thus, the water content can be as little as 20% and preferably from about 30 to 90%.

The dyeing compositions of this invention are preferably aqueous compositions. The term "aqueous composition" is used herein in its usual generic sense as embracing any water-containing composition embodied in the invention. This includes true solutions or mixtures of the dye in an aqueous medium, either alone or in conjunction with other materials, which are also dissolved or dispersed in the aqueous medium. The dye may be colloidally dispersed in the medium or may merely by intimately mixed therein.

To further illustrate the various other modifiers, antioxidants, alkalizers and other adjuvants that may be incorporated in the oxidation dye mixture of this invention, reference is made to Sagarin "Cometics, Science and Technology" (1957), 505–507, Interscience Publishers, Inc., New York. The aqueous compositions of this invention may take many forms. Thus, they may be thin or thick flowable liquids, pastes, creams, gels, etc.

To summarize the various components that may comprise the oxidation dye mixture of this invention, Table I below is given. The percentages are given as percent by weight based on the total weight of the oxidation dye mixture.

TABLE I

| Components | % by weight General | Preferred |
|---|---|---|
| New "para component" | 0.1 to 6 | 0.2 to 4 |
| Other "para component" | 0 to 5 | 0 to 3 |
| Coupling component | 0.1 to 6 | 0.2 to 4 |
| Other oxidation dye intermediate | 0 to 4 | 0.1 to 2 |
| Nitro dyes | 0 to 3 | 0.01 to 2 |
| Soap | 0 to 35 | 15 to 25 |
| Surfactant | 0 to 30 | 1 to 10 |
| Thickening agent | 0 to 5.0 | 0.05 to 3 |
| Antioxidants | 0 to 1.0 | 0.05 to 1 |
| Organic solvents | 0 to 40 | 5 to 30 |
| Water QS to | 100% | |
| Alkalizing agent to pH | 8 to 11 | 9 to 10 |

The aforesaid oxidation dye mixtures of this invention are intended for use in conjunction with conventional oxidation dye "developers," which contain the oxidizing agent necessary to effect reaction to colored products. Typical developers that are useful for this purpose are aqueous solutions of hydrogen peroxide, e.g. 5 to 12%, or high viscosity creams containing in addition, for example, nonylphenol polyethylene glycol or lauryl alcohol polyethylene glycol, in an amount of from 2–10% of the weight of developer, or crystalline peroxide such as urea peroxide or melamine peroxide.

In use, a quantity of the developer described above is mixed with a quantity of oxidation dye composition described previously. Usually, the amount of developer taken is far in excess of that required to oxidize the intermediates, the amounts taken being dependent on the form and concentration of the developer selected. The mixture is well shaken and applied to hair. It can be applied as a shampoo to the entire head, applied to one area of the hair, such as the roots and combed through the rest of the hair later. The mixture is allowed to remain on the head for a period of time and is then removed by shampooing. The normal time of application is 20–30 minutes, but application times of from 10 minutes to 1 hour can be used.

In one form of application of the compositions of this invention, the oxidation dye mixture is dispensed from an aerosol container under pressure of a suitable propellant. The foam so obtained is mixed with the developer, generally a solution of hydrogen peroxide, and applied to the hair as above.

In a preferred form of application, the oxidation dye mixture is dispensed from an aerosol container simultaneously with an aqueous solution of hydrogen peroxide. Such co-dispensing aerosol systems are well known and are described for example in Paul A Sanders' "Principles of Aerosol Technology" (Van Nostrand Reinhold Co., New York 1970), pages 347–350. In the co-dispensing system the oxidation dye mixture is stored in the outer chamber of the can together with the propellant, while the developer is stored in the inner chamber, both chambers emptying through a common valve simultaneously. The effluent foam is then applied directly to the hair as above. As propellants in this system one may use nitrogen, nitrous oxide, the volatile hydrocarbons such as butane, isobutane, or propane, or preferably the fluorinated hydrocarbons (commonly sold as Freons by the DuPont Co.) such as dichlorodifluoromethane; 1,1-difluoroethane; 1,2-dichloro-1,1,2,2-tetrafluoroethane, or 1-chloro-1,1-difluoroethane; mixtures of two or more hydrocarbons or fluorinated hydrocarbons may be used. The quantity of propellant used will generally be 3 to 10% of the chemical contents of the can (oxidation dye mixture and developer), and preferably 4 to 6%.

The following Examples are given to further illustrate the present invention. It is to be understood however, that this invention is not limited thereto.

The following terms used to define materials employed in the Examples and elsewhere in this case, have the following significances:

Carbopol 934 is a water soluble polymer of arcylic acid cross linked with about 1% of a polyallyl ether of sucrose having an average of about 5.8 allyl groups for each molecule of ether and having a molecular weight in the order of magnitude of 1,000,000;

Hydroxyethylcellulose - (Cellosize W.P. 40 L viscosity range) is hydroxyelthylated cellulose having a degree of substitution (D.S.) of from about 0.9 to 1.0 and a Hoeppler Viscosity of 80–112 cps at 20° C.

Carboxymethylcellulose is sodium carboxymethylcellulose having a viscosity of 1300–2200 cps at 25° C and at a concentration of 1% and a degree of substitution (D.S.) of from about 0.65 to 0.85 (Hercules CMC-7XP).

EXAMPLE 1

Preparation of N-ethyl-N-hydroxyethyl-p-phenylenediamine

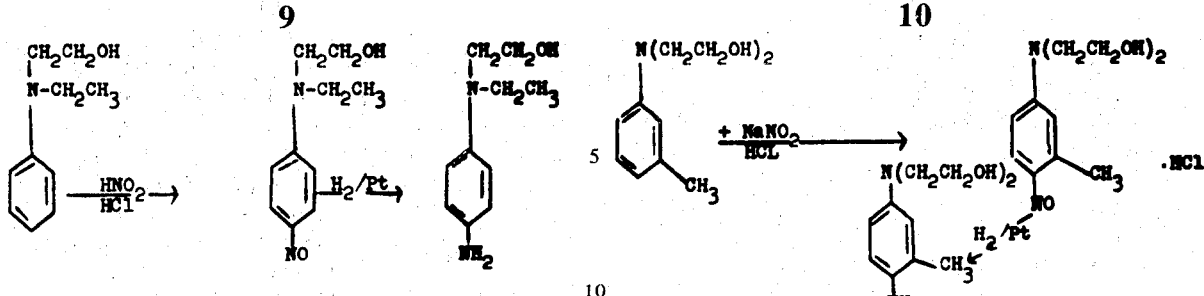

16.5 g of N-ethylanilinoethanol were dissolved in 75 ml conc. HCl and cooled to 0°C. 7.5 g of NaNO₂ in 20 ml of water were added with constant stirring, and at a rate to keep the temperature below 5°C. After the addition was complete, the mixture was allowed to stand for one hour more and the orange crystals formed were filtered and washed with 2M HCl in ethanol. The solid was dried in a vacuum desiccator overnight. Wt = 12.9 g.

The entire 12.9 g yield of 4-nitroso-N,ethyl-N-hydroxyethylaniline was dissolved in isopropanol and reduced in a Parr Hydrogenator over Pt/C. The mixture was filtered and HCl gas was bubbled through for 20 minutes. The reaction mixture was allowed to cool in a refrigerator overnight. The gray precipitate of N-ethyl-N-hydroxyethyl-p-phenylenediamine hydrochloride was collected. Yield 11.4 g.

EXAMPLE 2

Preparation of N,N-bis-(β-hydroxyethyl)-p-phenylenediamine

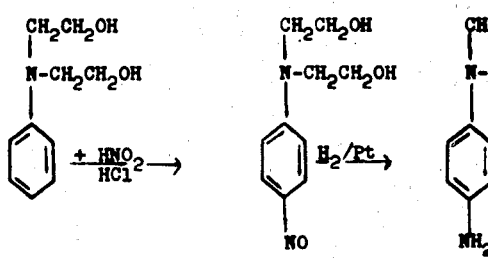

23.9 g of N-phenyldiethanol amine were ground in a mortar and dissolved in 50 ml conc. HCl. The solution was then cooled to 0°C and 10 g NaNO₂ in 25 ml of water were added over a period of one hour with stirring. The temperature was maintained between 0°–5°C. After the addition was complete, the mixture was stirred one hour more and then filtered. The orange precipitate of 4-nitroso-N,N-bis-(β-hydroxyethyl) aniline formed was dried in a vacuum desiccator overnight. The dried product, amounting to 25.0 g was suspended in 150 ml. isopropanol and reduced on a Parr hydrogenator over Pt/C. When the loss in pressure approached theoretical, the mixture was filtered into a flask containing 200 ml. isopropanol saturated with HCl gas. A stream of HCl gas was passed through the filtrate during the filtration and for about 20 minutes after the filtration was complete. The white precipitate of N,N-bis-(β-hydroxyethyl)-p-phenylenediamine hydrochloride was collected and weighed. Yield 19.8 g.

EXAMPLE 3

Preparation of N,N-bis-(β-hydroxyethyl)-3-methyl-p-phenylenediamine 25.38 g (13 M) of 2,2'm-tolyliminodiethanol was dissolved in 50 ml HCl and cooled to 0°C. 10 g NaNO₂ in 21 ml of water was added dropwise over a period of an hour with constant stirring at 0°–5°C. The solution changes from clear yellow to reddish orange to a thick yellow orange paste. After stirring one hour more, the material was filtered, washed twice with ethyl alcohol and dried under vacuum desiccator. Yield was 45.3 g of yellow crystals.

The nitrosoanilime prepared above was placed in 200 ml. isopropanol on the large Parr hydrogenator and reduced overnight. The resulting mixture was filtered and the filtrate treated with HCl gas to precipitate the product as the hydrochloride.

EXAMPLE 4

Preparation of N,3-Dimethyl-p-phenylenediamine

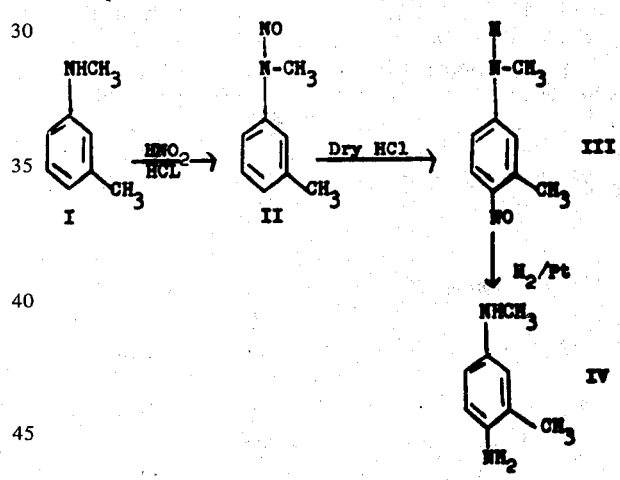

A mixture of 12.1 g N-methyl-m-toluidine (I) 14.5 g conc. HCl and 40 g of ice were stirred while 7 g NaNO₂ were added over a period of 5 minutes. The mixture was cooled externally and small portions of ice were added when needed to keep the temperature below 10°C. The mixture was allowed to stand at 0°C for 1 hour after the addition was complete and the oily top layer formed was separated. The lower aqueous layer was then extracted twice with 10 ml portions of benzene and the combined organic layers were distilled under reduced pressure. The material which boiled at 132°–138°C/8mm Hg was collected and dissolved in ethanol. Dry HCl gas was passed through this solution which heated up and deposited a precipitate of N,2-dimethyl-4-nitrosaniline (III) as the hydrochloride salt. The 16 g of product were suspended in isopropanol and reduced over Pt/C on a Parr hydrogenator. The reduction mixture was filtered and the catalyst was extracted with water. The combined filtrates were evaporated to dryness to yield 8 g of the product N,3-dimethyl-p-phenylenediamine hydrochloride.

EXAMPLE 5

Preparation of N-hydroxyethyl-2-methyl-p-phenylenediamine

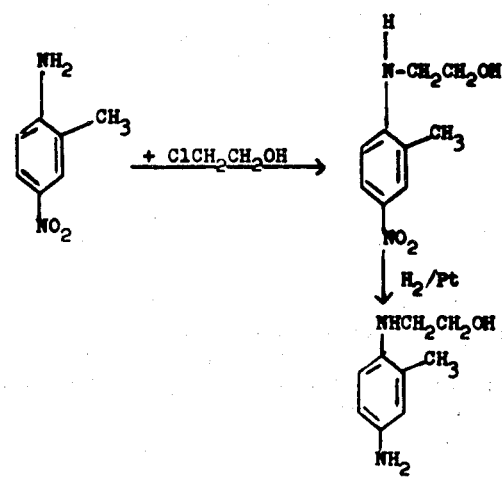

15.2 g of 2-methyl-4-nitroaniline was heated in an autoclave together with 8.05g of chloroethanol and 5.3g of sodium carbonate for 4 hours at 150°C. The mixture was then removed from the autoclave by dissolving it in methanol. The methanol was evaporated to small volume (about 25 ml) and water was added to precipitate the 4-nitro-2-methyl-N-hydroxyethylaniline. The precipitate was oily and weighed 12.7 g.

The entire precipitate was then dissolved in 150 ml of isopropanol and reduced on a Parr hydrogenator over Pt/C. The resulting filtered solution was treated with dry HCl gas to give 14.1 g of a blue precipitate of N-hydroxyethyl-2-methyl-p-phenylenediamine hydrochloride.

EXAMPLE 6

Preparation of N,2-dimethyl-p-phenylenediamine

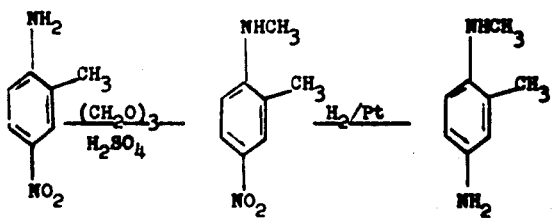

15.2 g of 2-methyl-4-nitroaniline were dissolved in 150 ml conc. $H_2SO_4$ and heated in a boiling water bath. To this solution 24 g. of paraformaldehyde were added with stirring over a period of 10 minutes. The mixture was stirred an additional hour and was then cooled and poured over 300 g of ice. The precipitate was recrystallized from ethanol water to give 10.1 g of N,2-dimethyl-4-nitroaniline (m.p. 133°–136°C).

The entire 10.1 g yield was reduced on a Parr hydrogenator in ethanol over Pt/C. The catalyst was filtered and the product precipitated by addition of an excess of conc. hydrochloric acid. There was obtained 9.2 g of a tan precipitate of N,1-dimethyl-p-phenylenediamine hydrochloride.

EXAMPLE 7

Preparation of N¹-methyl-3-methoxy-p-phenylenediamine

A mixture of 13.7 g of N-Methyl-3-methoxyaniline, 14.5 ml conc HCl and 40 g ice are stirred while 7 g $NaNO_2$ in 15 ml water added at 0°–5°C. After one hour the top layer of the solution is separated and the lower aqueous layer extracted with benzene. Benzene is removed from the combined organic layers by evaporation under reduced pressure and residue was distilled under vacuum. The distillate is taken up in dry ethanol and dry HCl gas is bubbled through the solution to precipitate solid 4-nitro-3-methoxy-N-methylaniline hydrochloride. This product is reduced over Pt/C on a Parr Hydrogenator to give the product.

The same procedure using 15.3 g of 3-chloro-N-methylaniline in place of the N-methyl-3-methoxyaniline gives 3-chloro-N¹-methyl-p-phenylenediamine.

EXAMPLE 8

1 ounce of a solution of the following composition is prepared:

| | |
|---|---|
| N,N-bis(2-hydroxyethyl)-p-phenylenediamine hydrochloride | 1% |
| 2,4-diaminotoluene | 1% |
| oleic acid | 35% |
| ammonium hydroxide (28% Aq.) | 8% |
| isopropanol | 20% |
| water | 41% |

This solution is mixed with 1 oz. of 6% aqueous hydrogen peroxide and applied to a swatch of gray hair for 20 minutes at ambient temperature. The hair is found to be dyed a blue shade and the color is very stable to the effect of sunlight and acid and alkaline perspiration.

EXAMPLE 9

1 ounce of a solution of the following composition:

| | |
|---|---|
| 2,6-dimethyl-p-phenylenediamine | .5% |
| N,N-bis(2,3-dihydroxypropyl)-p-phenylenediamine | .1% |
| resorcinol | .6% |
| 2,4-diaminoanisole sulfate | .1% |
| 4-nitro-o-phenylenediamine | .1% |
| 2-nitro-p-phenylenediamine | .1% |
| Hydroxyethylcellulose | 1% |
| ammonium acetate | 4% |
| 28% aqueous ammonia | 10% |
| ammonium lauryl sulfate | .1% |
| water | 92% | is mixed with 1 oz of 6% aqueous hydrogen peroxide and applied to gray hair for 20 minutes. The hair is found to be dyed light brown and the color is stable to the effects of sunlight and of acid perspiration.

EXAMPLE 10

1 ounce of a solution of the following composition:

| | |
|---|---|
| N,2-dimethyl-p-phenylenediamine | 3.2% |
| resorcinol | 2.1% |
| m-phenylenediamine | .2% |
| o-phenylenediamine | .4% |
| 2-nitro-p-phenylenediamine | .2% |
| Carbopol 934 | 1.5% |
| ammonium acetate | 5% |
| ammonia (28% aqueous) | 12% |
| isopropanol | .5% |
| sodium lauryl sulfate | .2% |
| sodium sulfite | 0.7% |
| water | 83.5% | is mixed with 1 oz of 6% aqueous $H_2O_2$ containing 1% Carbopol 934 and applied to gray hair for 20 minutes.

The hair is found to be dyed dark brown and the color is stable to acid perspiration and to sunlight.

EXAMPLE 11

1 ounce of a solution of the following composition:

| | |
|---|---|
| 4-amino-2-methyl-N-(2-hydroxyethyl)-aniline hydrochloride | 3.5% |
| resorcinol | 3.5% |
| 2,4-diaminoanisole sulfate | .2% |
| nitro-p-phenylenediamine | .1% |
| 4-nitro-o-phenylenediamine | .1% |
| oleic acid | 12% |
| ammonia | 1.5% |
| isopropanol | 7.5% |
| sodium lauryl sulfate | .1% |
| water | 71.5% | is mixed with 1 oz. of a solution of 1% Carbopol 934 in 6% aqueous hydrogen peroxide. The mixture is applied to gray hair for 30 minutes and produces a brown shade which is stable to perspiration and sunlight.

EXAMPLE 12

1 oz. of a solution of the following composition:

| | |
|---|---|
| N,3-dimethyl-p-phenylenediamine hydrochloride | 1.2% |
| resorcinol | 1.3% |
| m-phenylenediamine | .1% |
| nitro-p-phenylenediamine | .05% |
| oleic acid | 5% |
| diethanolamine | 2% |
| isopropanol | 5% |
| glycerine | .2% |
| water to | 100% | was mixed with 1 oz. of 6% aqueous hydrogen peroxide containing 1% hydroxyethylcellulose. The mixture was applied to gray hair for 30 minutes and then removed by shampooing. The hair was found to be dyed a very light brown and the color was relatively resistant to perspiration and sunlight.

EXAMPLE 13

1 oz. of solution of the following composition:

| | |
|---|---|
| N-methyl-2-methoxy-p-phenylene-diamine | 3.5% |
| resorcinol | 3.3% |
| 2,4-diaminoanisole sulfate | .1% |
| o-phenylenediamine | .5% |
| 4-nitro-o-phenylenediamine | .05% |
| 28% aqueous ammonia | 10% |
| ammonium acetate | 2.5% |
| water | 89.5% | was mixed with 0.5 oz. of 6% aqueous $H_2O_2$ and applied to a swatch of gray hair for 20 minutes. The dye was removed by rinsing and the hair on drying was found to be dyed a medium yellow-brown shade. The color was resistant to acid perspiration and sunlight.

EXAMPLE 14

One-half oz. of a solution of the following composition:

| | |
|---|---|
| p-phenylenediamine | 2.5% |
| resorcinol | 2.5% |
| N,N-bis-(β-hydroxyethyl)-3-methyl-p-phenylenediamine sulfate | 0.5% |
| 2,4-diaminoanisole | .2% |
| o-phenylenediamine | .7% |
| nitro-p-phenylenediamine | .1% |
| Carbopol 934 | 2% |
| 28% aqueous ammonia | 12% |
| sodium sulfite | 1.1% |
| sodium lauryl sulfate | .2% |
| water | 88.5% | is mixed with 1½ oz. of 4% aqueous hydrogen peroxide and applied to gray hair for 30 minutes. The hair is found to be dyed a medium brown shade and the color is relatively stable to acid perspiration and to sunlight.

EXAMPLE 15

A solution of the following composition:

| | |
|---|---|
| N,N-bis (β-hydroxyethyl)-3-methyl-p-phenylenediamine | .6% |
| p-phenylenediamine | 1.5% |
| resorcinol | 2.0% |
| 2,4-diaminotoluene | .5% |
| o-phenylenediamine | .25% |
| sodium acetate | 10% |
| ammonium hydroxide 28% | 10% |
| sodium lauryl sulfate | .25% |
| water to 100% | | was mixed with an equal volume of a solution of 1% carboxymethylcellulose in 6% aqueous $H_2O_2$. The mixture is applied to gray hair for 20 minutes and produces a stable violet-brown color.

EXAMPLE 16

A mixture of the following composition:

| | |
|---|---|
| N-ethyl-N-hydroxyethyl-p-phenylenediamine hydrochloride | 3.5% |
| resorcinol | 3.5% |
| 2,4-diaminoanisole sulfate | .2% |
| nitro-p-phenylenediamine | 0.1% |
| 4-nitro-o-phenylenediamine | 0.1% |
| ammonia as free base | 2.4% |
| Carbopol 934 | 1% | is mixed with an equal volume of 6% aqueous $H_2O_2$ and applied to gray hair for 25 minutes. The hair is dyed a stable brown shade.

EXAMPLE 17

An oxidation dye composition is prepared of the following ingredients, in the weight percentages given:

| | |
|---|---|
| p-phenylenediamine | 2.6% |
| N,N-bis-(2-hydroxyethyl)-p-phenylenediamine sulfate | 0.4% |
| resorcinol | 1.0% |
| 2,4-diaminoanisole sulfate | 0.7% |
| 4-Nitro-o-phenylenediamine | 0.06% |
| o-aminophenol | 0.15% |
| m-aminophenol | 0.3% |
| ethylenediamine tetraacetic acid | 0.04% |
| isopropanol | 10% |
| ammonium hydroxide 28% | 9% |
| sodium lauryl sulfate | 2.5% |
| sulfonated castor oil | 2.8% |
| carbitol (diethyleneglycol ethyl ether) | 4% |
| oleic acid | 15% |
| propylene glycol | 4% |
| water to make 100% | |

Three ounces of the above composition is loaded into a co-dispensing aerosol can which employs the "OEL co-dispensing valve," as described in Sanders, "Principles of Aerosol Technology," pages 348–349.

The inner compartment (peroxide bag), a flexible polyethylene bag, is filled with the developer solution namely one ounce of 12% aqueous hydrogen peroxide, and the can is sealed with the introduction of 4.5 g of a propellant consisting of 35% 1,2-dichloro-1,1,2,2-tetrafluoroethane and 65% 1,1-difluoroethane. For application to hair the contents of the can are released as a foam consisting of an intimate mixture of the oxidation dye mixture and the developer in the ratio of 3:1. The foam is worked into the hair and is left on for twenty minutes, after which the hair is thoroughly rinsed. It is dyed a deep black which remains little changed in shade or strength on being worn for six weeks with shampooing approximately every week.

Unless otherwise specified all of the dyeings carried out in the above examples are carried out at room temperature.

What is claimed is:

1. A non-toxic oxidation hair dye composition comprising an aqueous carrier, as a para component from about .1% to 6% by weight based on the total weight of the composition of a compound of formula:

(a) 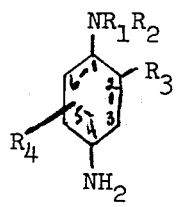

or acid addition salts thereof and b. from about 0.1% to 8% by weight based on the total weight of the composition of an oxidatively couplable component comprising a phenol which couples with said para component to give blue or violet compounds wherein:

$R_1$ is hydroxyalkyl;
$R_2$ is hydrogen or hydroxyalkyl;
$R_3$ is hydrogen, alkyl, alkoxy or halogen; and
$R_4$ occupies any one of the remaining positions on the benzene ring and is hydrogen, alkyl, alkoxy or halogen;
and wherein the alkyl or alkoxy contains 1 to 6 carbon atoms and the hydroxyalkyl contains 2 to 6 carbon atoms;
providing that $R_2$ is hydrogen when $R_3$ is alkyl, alkoxy or halogen;
and providing that at least two of $R_2$, $R_3$ or $R_4$ are other than hydrogen.

2. A non-toxic oxidation hair dye composition comprising an aqueous carrier, as a para component from about 0.1% to 6% by weight based on the total weight of the composition of a compound of formula:

(a) 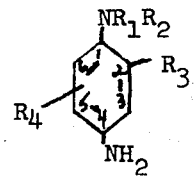

or acid addition salts thereof and b. from about .1% to 8% by weight based on the total weight of the composition of an oxidatively couplable component comprising a phenol which couples with said para component and is selected from the group consisting of pyrogallol, resorcinol, pyrocatechol and alpha-naphthol wherein:

$R_1$ is hydroxyalkyl;
$R_2$ is hydrogen or hydroxyalkyl;
$R_3$ is hydrogen, alkyl, alkoxy or halogen; and
$R_4$ occupies any one of the remaining positions on the benzene ring and is hydrogen, alkyl, alkoxy or halogen;
and wherein the alkyl or alkoxy contains 1 to 6 carbon atoms and the hydroxyalkyl contains 2 to 6 carbon atoms;
providing that $R_2$ is hydrogen when $R_3$ is alkyl, alkoxy or halogen;
and providing that at least two of $R_2$, $R_3$ or $R_4$ are other than hydrogen.

3. A composition according to claim 2 wherein said phenol is alpha-naphthol.

4. A composition according to claim 2 wherein $R_1$ and $R_2$ are hydroxyalkyl and $R_3$ and $R_4$ are hydrogen.

5. A composition according to claim 4 wherein $R_1$ and $R_2$ are 2-hydroxyethyl.

6. A composition according to claim 2 wherein $R_1$ is hydroxyalkyl, $R_2$ is hydrogen, $R_3$ is alkyl and $R_4$ is hydrogen.

7. A composition according to claim 6 wherein $R_1$ is 2-hydroxyethyl and $R_3$ is methyl.

8. A composition according to claim 2 wherein $R_1$ and $R_2$ are hydroxyalkyl, $R_3$ is hydrogen and $R_4$ is alkyl which occupies position number 3 on the benzene nucleus.

9. A composition according to claim 8 wherein $R_1$ and $R_2$ are 2-hydroxyethyl and $R_4$ is methyl which occupies position number 3 on the benzene nucleus.

10. A composition according to claim 2 in which both $R_1$ and $R_2$ are 2-hydroxyethyl.

11. A composition according to claim 2 wherein said para component is N,N-bis(2-hydroxyethyl)-p-phenylenediamine sulfate and said phenol is alpha-naphthol.

12. A composition according to claim 2 including as an additional para component a compound selected from the group consisting of p-toluenediamine, p-aminophenol, p-aminodiphenylamine; 4,4'-diaminodiphenylamine; p-phenylenediamine; 2,6-dimethyl-p-phenylenediamine and 2,5-diaminopyridine.

13. A composition according to claim 12 wherein $R_1$ and $R_2$ are 2-hydroxyethyl, $R_3$ and $R_4$ are hydrogen and also containing p-phenylenediamine.

14. A composition according to claim 12 wherein $R_1$ and $R_2$ are 2-hydroxyethyl, $R_3$ and $R_4$ are hydrogen and wherein the additional para component is p-toluenediamine.

15. A method for dyeing hair which comprises applying the composition of claim 2 with an oxidizing agent to the hair until the hair is dyed.

* * * * *